(12) United States Patent  (10) Patent No.: US 6,709,435 B2
Lin  (45) Date of Patent: Mar. 23, 2004

(54) THREE-HOOKED DEVICE FOR FIXING SPINAL COLUMN

(75) Inventor: Chih-I Lin, Chino Hills, CA (US)

(73) Assignee: A-Spine Holding Group Corp., Tortola (VG)

( * ) Notice: Subject to any disclaimer, the term of this patent is extended or adjusted under 35 U.S.C. 154(b) by 184 days.

(21) Appl. No.: 10/107,402

(22) Filed: Mar. 28, 2002

(65) Prior Publication Data

US 2003/0187435 A1 Oct. 2, 2003

(51) Int. Cl.$^7$ .............................................. A61B 17/56
(52) U.S. Cl. .............................. 606/61; 606/72; 606/74
(58) Field of Search ............................. 606/61, 69, 70, 606/71, 72, 74

(56) References Cited

U.S. PATENT DOCUMENTS

| 3,824,995 | A | * | 7/1974 | Getscher et al. | 606/69 |
| 5,002,542 | A | * | 3/1991 | Frigg | 606/61 |
| 5,439,463 | A | * | 8/1995 | Lin | 606/61 |
| 5,941,881 | A | * | 8/1999 | Barnes | 606/71 |
| 6,136,000 | A | * | 10/2000 | Louis et al. | 606/61 |
| 6,387,097 | B1 | * | 5/2002 | Alby | 606/61 |
| 6,641,585 | B2 | * | 11/2003 | Sato et al. | 606/61 |
| 2002/0169451 | A1 | * | 11/2002 | Yeh | 606/61 |
| 2003/0045876 | A1 | * | 3/2003 | Stahurski | 606/61 |
| 2003/0109882 | A1 | * | 6/2003 | Shirado et al. | 606/61 |
| 2003/0109883 | A1 | * | 6/2003 | Shirado et al. | 606/61 |

* cited by examiner

Primary Examiner—Pedro Philogene
Assistant Examiner—David A Bonderer
(74) Attorney, Agent, or Firm—Bacon & Thomas, PLLC

(57) ABSTRACT

A spine fixing device includes a main hooked seat, two extension hooks, and two fastening members. The main hooked seat is provided with a main hooked portion, two extension arms, and two fastening rods for fastening two fixation rods of the prior art. The extension hook is provided at one end with a curved portion, and at other end with an adjustment portion which is fastened with one of the two extension arms of the main hooked seat by one of the two fastening members. The device is retained in the back of one spinal segment such that the main hooked portion is inserted into a portion of the spinal canal of the spinal segment, and that the extension arms embrace the spinal projection of the spinal segment, and further that the curved portions of the extension hooks catch two different portions of the spinal canal of the spinal segment from the opposite direction.

6 Claims, 4 Drawing Sheets

THREE-HOOKED DEVICE FOR FIXING SPINAL COLUMN

FIELD OF THE INVENTION

The present invention relates generally to a device for fixing a spine under treatment, and more particularly to a there-hooked device which is retained in the back of one spinal segment to facilitate the fixing of the spine.

BACKGROUND OF THE INVENTION

There are a variety of conventional devices for use in fixing an injured or deformed vertebra. For example, the Halifax Tx Inter/aminar Clamp System of THE AME Corp. of the U.S. comprises a fastening bolt and a nut by means of which the spinal fixation is done. The spinal fixation effect of this prior art clamp system is poor in view of the fact that the nut is apt to become unfastened with the fastening bolt due to the intervertebral stress.

With the view of overcoming the deficiency of the prior art device described above, this inventor of the present invention developed two spinal fixation devices, which are respectively disclosed in the U.S. Pat. Nos. 5,454,812 and 5,380,326.

In light of lack of a spinal fixation device which is designed to fix only one spinal segment so as to facilitate the spinal surgery, this inventor of the present invention developed a vertebral fixation device, which is disclosed in the U.S. Pat. No. 5,507,747. This device is complicated in design in that it is formed of many component parts. In other words, the device tends to complicate and prolong the surgical operation, especially in a situation calling for treatment of multiple vertebrae.

SUMMARY OF THE INVENTION

It is the primary objective of the present invention to provide a three-hooked device for fixing one spinal segment. The three-hooked device comprises a main hooked seat and two extension hooks. The fixation of one spinal segment is attained by a main hooked portion of the main hooked seat and one hooked end of the two extension hooks.

It is another objective of the present invention to provide a three-hooked device for fixing any one of the spinal segments. The three-hooked device comprises a main hooked seat which is provided with two fastening rods extending therefrom for fixing the spinal segment in conjunction with the conventional fastening members, such as fixation rod, fixation screw, and the like.

In keeping with the principle of the present invention, the foregoing objectives of the present invention are attained by a three-hooked device comprising a main hooked seat, two extension hooks, and two fastening members. The main hooked seat is provided on one side near the undersurface with a main hooked portion, and near the uppersurface with two extension arms. The main hooked seat is further provided with two fastening rods extending therefrom. The main hooked seat serves to retain the spinal segment in such a manner that the main hooked portion is inserted into the spinal canal of the spinal segment, and that the two extension arms embrace the spinal projection of the spinal segment. The two extension hooks are provided at one end with a curved portion, and at other end with an adjustment portion. The curved portion serves to catch the spinal canal of the spinal segment, whereas the adjustment portion is adjustably fastened with the extension arm of the main hooked seat by the fastening member. The fastening member is formed of a sleeve and a tightening piece for fixing securely the adjustment portion which is adjustably received in the sleeve along with the extension arm.

In operation, the device of the present invention is retained in the back of any one of the spinal segments such that the main hooked portion of the main hooked seat and the curved portions of the two extension hooks hold the spinal canal of the spinal segment, and that the two fastening rods of the main hooked seat are fastened with the conventional fixation rods or fixation screws.

The component parts of the device of the present invention are made of a metal material implantable in the human body, such as the iron-based stainless steel 316 LVM (stainless steel 316 LUM), the titanium-based material Ti-6-4, the cobalt-molybdenum-chromium allow etc.

The features and the advantages of the present invention will be more readily understood upon a thoughtful deliberation of the following detailed description of a preferred embodiment of the present invention with reference to the accompanying drawings.

DETAILED DESCRIPTION OF THE EMBODIMENTS

Figure 1:
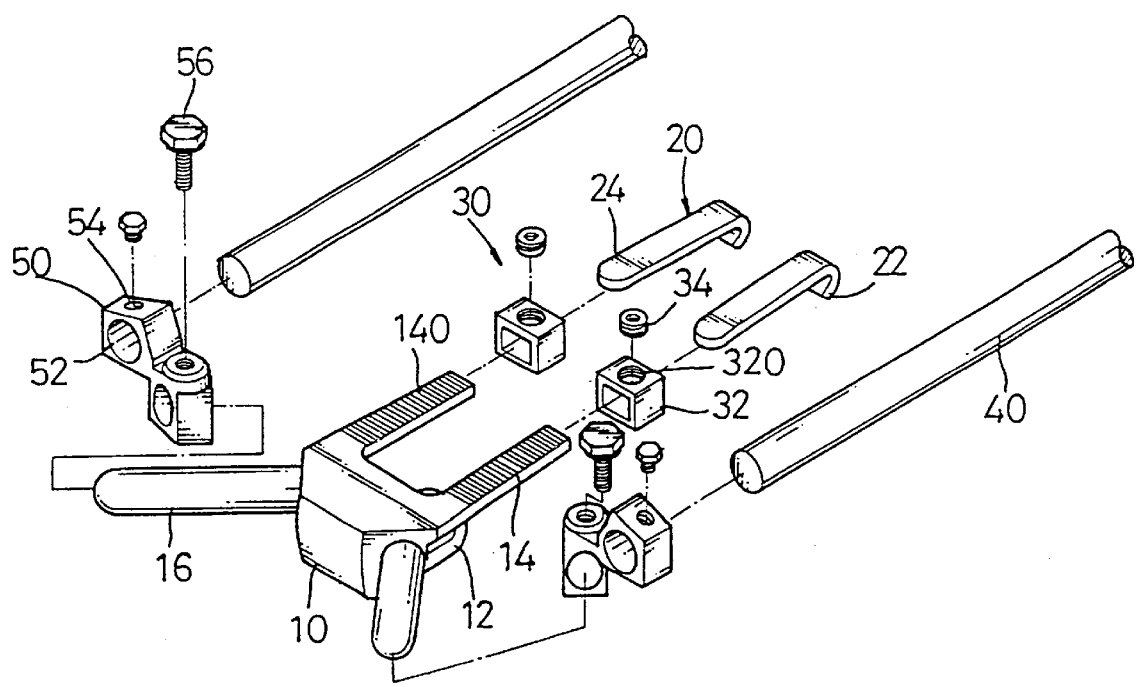
FIG. 1 shows an exploded view of the preferred embodiment of the present invention.
Figure 2:
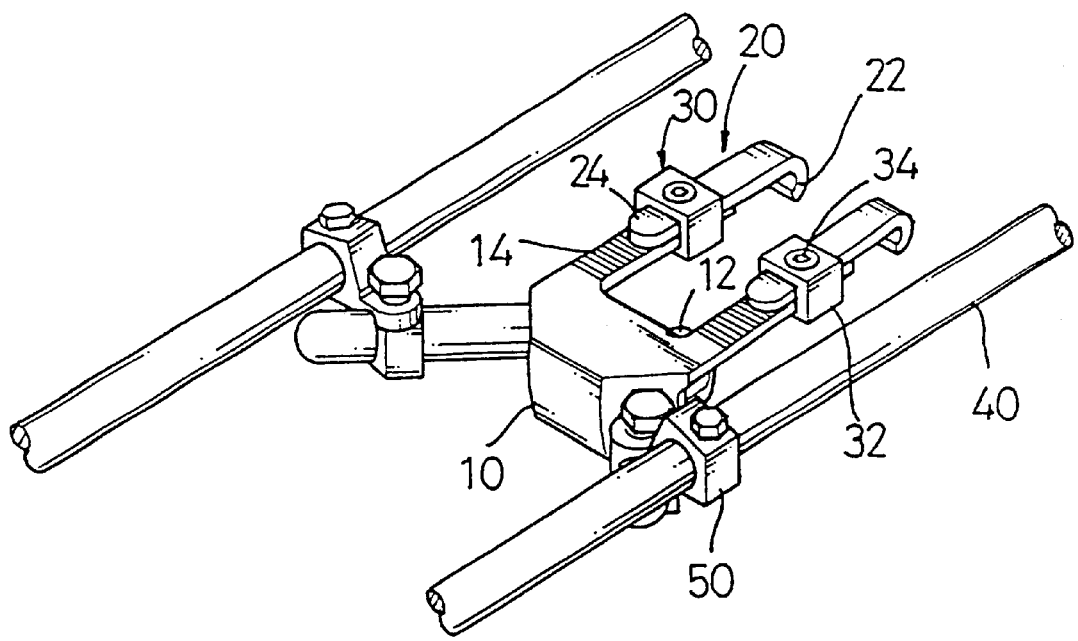
FIG. 2 shows a perspective view of preferred embodiment of the present invention in combination.

As shown in FIGS. 1 and 2, a three-hooked device embodied in the present invention comprises a main hooked seat 10, two extension hooks 20, and two fastening members 30.

The main hooked seat 10 is provided on one side near the undersurface with a main hooked portion 12, and near the uppersurface with two extension arms 14 extending in the same direction at an interval. The extension arms 14 are provided on the upperside with a knurled portion 140. The main hooked seat 10 is further provided with two fastening rods 16 extending from locations opposite to the two extension arms 14.

The two extension hooks 20 are provided at one end with a curved portion 22, and at other end with an adjustment portion 24 which is provided on the underside with a knurled portion (not shown in the drawings).

The two fastening members 30 are formed of a sleeve 32 and a tightening piece 34. The sleeve 32 is provided with a threaded hole 320 engageable with the tightening piece 34. The fastening members 30 are used to fasten adjustably the extension hooks 20 with the extension arms 14 of the main hooked seat 10 such that the adjustment portion 24 of the extension hooks 20 and the extension arm 14 of the main hooked seat 10 are received in the sleeve 32, and that the knurled portion 140 of the extension arm 14 is in contact with the knurled portion of the adjustment portion 24 of the extension hooks 20, and further that the adjustment portion 24 is tightened against the extension arm 14 by the tightening piece 34 which is engaged with the threaded hole 320 of the sleeve 32.

In operation, the three-hooked device of the preferred embodiment of the present invention is employed in conjunction with two fixation rods 40 of a device disclosed in the U.S. Pat. No. 5,582,612 which was issued to this inventor of the present invention. The two fixation rods 40 are coupled with the two fastening rods 16 of the main hooked seat 10 by two coupling members 50. The coupling member 50 has two through holes 52 for receiving the fixation rod 40 and the fastening rod 16 respectively, and has two threaded holes 54 perpendicular to the through holes 52. The coupling member 50 is fastened with the fastening rod 16 of the main hooked seat 10 by inserting the fastening rod 16 into the through hole 52 at one end of the coupling member 50 and threading a fastening screw 56 into the corresponding threaded hole 54, and then the fixation rod 40 is inserted into the through hole 52 at another end of the coupling member and is tightened by a tightening piece which is engaged with the corresponding threaded hole 54.

Figure 3:
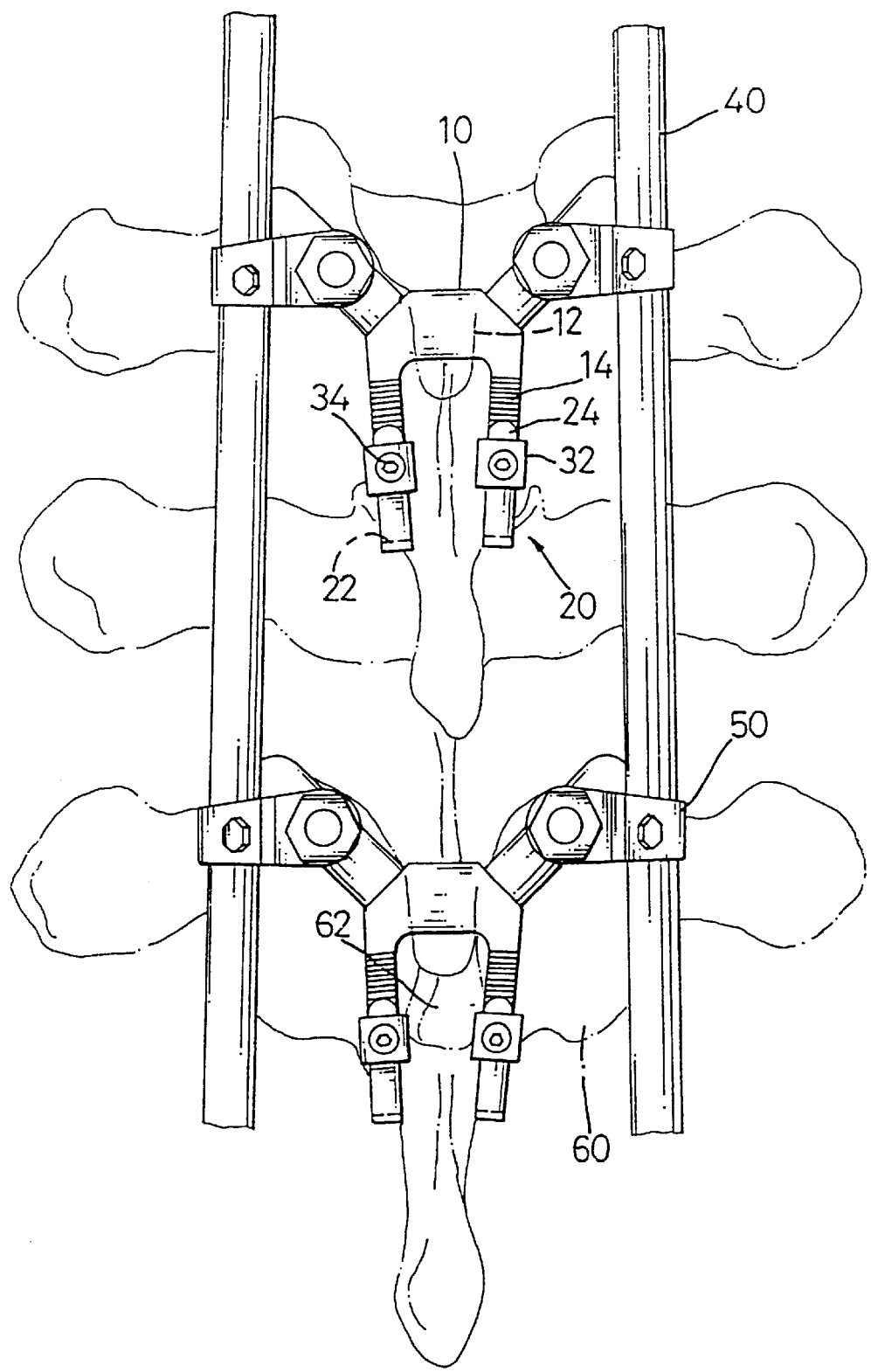
FIG. 3 shows a schematic plan view of the preferred embodiment of the present invention being fastened to the back of the spinal segments.
Figure 4:
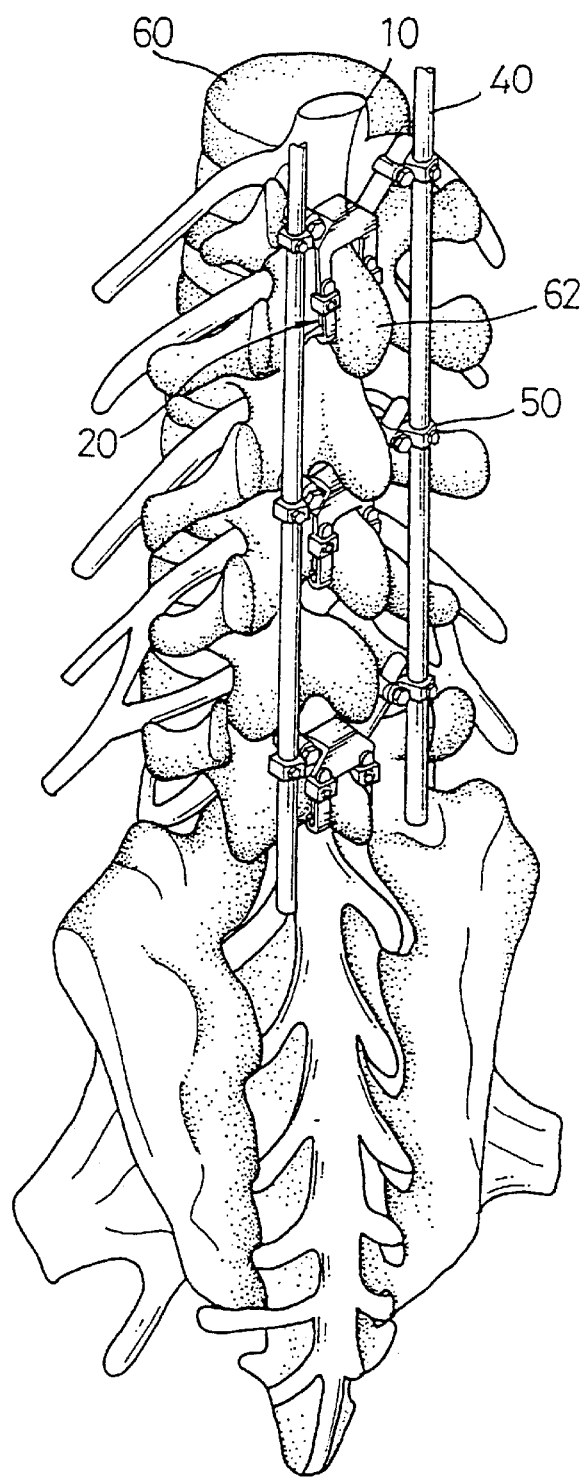
FIG. 4 shows a perspective view of preferred embodiment of the present invention being fastened to the back of the lumbar vertebrae.

As illustrated in FIGS. 3 and 4, the device of the present invention is used in the surgical operation in such a manner that the main hooked seat 10 is located between two spinal segments 60, and that the main hooked portion 12 is inserted into the spinal canal of one of the two spinal segments 60, and that the two extension arms 14 of the main hooked seat 10 embrace the spinal projection 62 of that one spinal segment 60. Thereafter, the sleeves 32 of the fastening members 30 are respectively fitted over the extension arms 14 before the curved portion 22 of the extension hooks 20 catches a portion of the spinal canal of that one spinal segment 60, with the portion being separated from an insertion portion into which the main hooked portion 12 was previously inserted. The adjustment portion 24 of the extension hooks 20 is inserted into the sleeve 32 such that the knurled portion of the underside of the adjustment portion 24 comes in contact with the knurled portion 140 of the extension arm 14, and that the adjustment portion 24 is tightened against the extension arm 14 by the tightening piece 34 which is engaged with the threaded hole 320 of the sleeve 32. The fixation rods 40 are coupled with the device of the present invention in conjunction with the coupling members 50. It is suggested that the two extension hooks 20 and the main hooked seat 10 are kept as closely as possible, so as to enhance the clamping effect on the same spinal segment 60.

What is claimed is:

1. A spine fixing device comprising:
   a main hooked seat provided on one side near an undersurface with a main hooked portion, and near an uppersurface with two extension arms, said main hooked seat further provided with two fastening rods;
   two extension hooks provided at one end with a curved portion, and at other end with an adjustment portion; and
   two fastening members for fastening said extension arms of said main hooked seat with said adjustment portions of said two extension hooks.

2. The spine fixing device as defined in claim 1, wherein each of said fastening members is formed of a sleeve and a tightening piece, said sleeve being provided with a threaded hole engageable with said tightening piece, wherein said sleeve receives said extension arm and said adjustment portion such that said adjustment portion is tightened against said extension arm by said tightening piece via said threaded hole of said sleeve.

3. The spine fixing device as defined in claim 2, wherein said extension arm of said main hooked seat is provided on an upperside thereof with a knurled portion; wherein said adjustment portion is provided on an underside with a knurled portion; wherein said extension arm and said adjustment portion are fastened in said sleeve such that said knurled portion of said extension arm comes in contact with said knurled portion of said adjustment portion.

4. The spine fixing device as defined in claim 1, wherein each of said two fastening rods of said main hooked seat is intended to fasten with a fixation rod.

5. The spine fixing device as defined in claim 4 further comprising two couplings members, each of which is for fastening the fixation rod to said fastening rod, wherein said coupling member is provided with a first through hole and a first threaded hole in communication with said first through hole, said first through hole being used to receive the fixation rod which is tightened by a first tightening piece via said first threaded hole of said coupling member; said coupling member is further provided with a second through hole and a second threaded hole in communication with said second through hole, said second through hole being used to receive the fastening rod which is tightened by a second tightening piece via said second threaded hole of said coupling member.

6. The spine fixing device as defined in claim 1, wherein said two extension arms extend from the hooked seat in the same direction at an interval, and said two fastening rods extend from locations opposite to the two extension arms.

\* \* \* \* \*